United States Patent
Mayer et al.

(10) Patent No.: US 10,457,463 B2
(45) Date of Patent: Oct. 29, 2019

(54) PROTECTIVE PACKAGING WITH MOUNTING AND REMOVAL FUNCTION

(71) Applicants: Markus Mayer, Lindau (DE); Stefan Brauchle, Wangen (DE); Thiemo Roesler, Wangen (DE)

(72) Inventors: Markus Mayer, Lindau (DE); Stefan Brauchle, Wangen (DE); Thiemo Roesler, Wangen (DE)

(73) Assignee: ROSE PLASTIC AG (DE)

( * ) Notice: Subject to any disclaimer, the term of this patent is extended or adjusted under 35 U.S.C. 154(b) by 493 days.

(21) Appl. No.: 15/046,512

(22) Filed: Feb. 18, 2016

(65) Prior Publication Data

US 2016/0244234 A1   Aug. 25, 2016

(51) Int. Cl.
| | |
|---|---|
| *B65D 81/02* | (2006.01) |
| *B65D 25/10* | (2006.01) |
| *B65D 85/20* | (2006.01) |
| *A61B 50/30* | (2016.01) |
| *A61B 50/00* | (2016.01) |

(52) U.S. Cl.
CPC .......... *B65D 81/02* (2013.01); *A61B 50/3001* (2016.02); *B65D 25/101* (2013.01); *B65D 85/20* (2013.01); *A61B 2050/005* (2016.02); *A61B 2050/006* (2016.02); *A61B 2050/0051* (2016.02); *A61B 2050/0056* (2016.02)

(58) Field of Classification Search
USPC ................. 206/349, 372, 373, 370; 81/177.4
See application file for complete search history.

(56) References Cited

U.S. PATENT DOCUMENTS

| | | | | |
|---|---|---|---|---|
| 4,921,096 A | * | 5/1990 | McFarlane .......... | A61M 25/002 206/349 |
| 5,413,223 A | * | 5/1995 | Kang ...................... | F21L 15/08 206/349 |
| 7,740,136 B2 | * | 6/2010 | Roesler .................. | B25H 3/003 206/379 |
| 8,783,459 B1 | * | 7/2014 | Marcinkowski ..... | B65D 5/5088 206/349 |
| 2006/0283769 A1 | * | 12/2006 | Roesler .................. | B25H 3/023 206/588 |
| 2008/0083304 A1 | | 4/2008 | Finn | |

(Continued)

FOREIGN PATENT DOCUMENTS

| | | |
|---|---|---|
| EP | 0383487 | 8/1990 |
| JP | 2001259964 | 9/2001 |

*Primary Examiner* — Jacob K Ackun
(74) *Attorney, Agent, or Firm* — Cohen & Grigsby, P.C.

(57) ABSTRACT

A protective packaging for sharp-edged objects is disclosed. The protective packaging generally has two shell parts connected pivotally on one side in the area of a pivot axis. At least one of the shell parts forms a first receiving space that is configured to receive an object and provide a free space between for the shell parts and the object, and a second receiving area configured to hold the object in a form-fitting manner. A third receiving space adjacent the second receiving area provides sufficient space for connection of a tool carrier to the object. The protective packaging is therefore designed as a mounting and removal tool rotatable around its longitudinal axis, and the object contained in the protective packaging can be mounted on and removed from any tool holder together with the protective packaging without contact with the hand.

15 Claims, 8 Drawing Sheets

(56) References Cited

U.S. PATENT DOCUMENTS

| | | | | |
|---|---|---|---|---|
| 2008/0185305 A1* | 8/2008 | Roesler | ............... | B65D 25/101 |
| | | | | 206/349 |
| 2008/0283430 A1* | 11/2008 | Huang | ................... | B25B 15/00 |
| | | | | 206/349 |
| 2009/0223329 A1* | 9/2009 | Hi | ......................... | B25G 1/066 |
| | | | | 81/177.8 |
| 2011/0088522 A1* | 4/2011 | Floyd | ..................... | B25B 15/00 |
| | | | | 81/438 |
| 2013/0020217 A1* | 1/2013 | Alexander | ......... | B65D 73/0071 |
| | | | | 206/349 |
| 2015/0068937 A1* | 3/2015 | Jiang | ..................... | B25H 3/003 |
| | | | | 206/349 |

\* cited by examiner

PROTECTIVE PACKAGING WITH MOUNTING AND REMOVAL FUNCTION

CROSS REFERENCE TO RELATED APPLICATIONS

The present application claims priority to German Patent Application No. 10 2015 002214.8, filed on Feb. 20, 2015, which is herein incorporated in its entirety by reference.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC OR AS A TEXT FILED VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

FIELD OF THE INVENTION

The invention relates to plastic packaging, and in particular, to packaging for protecting sharp-edged objects such as tools and instruments.

BACKGROUND OF THE INVENTION

Protective packaging of a general nature for packaging of items are known. In the case here, particularly sensitive items are to be protected against damage and/or contact by a protective packaging.

In the medical field, it is frequently necessary to protect work pieces or mounting means from hand contact or contamination by other objects.

In the medical field, mounting means such as screws, pins, medical mounting means and tools and the like must be protected from hand contact.

Such a protective packaging is shown by DE 10 2013 004 146 A1. It involves packaging for elongated objects with sharp edges, in particular for tools for surgical applications, which are in a packaging at least partially composed of plastic held in a secure position, the package consisting essentially of an enlarged packaging portion that consists of shell parts pivotally connected by a film hinge, which define a packaging portion as an interior into which the object to be protected and secured protrudes with its sharp-edged surfaces in a noncontact manner.

DE 10 2013 004 146 A1 already describes a protective packaging for the packaging of sharp-edged items like tools, instruments and the like by securing an object used in connection with a holder, where the protective packaging maintains the object in a secure position therein.

The two shell parts mounted pivotally to each other in the area of a longitudinal side are connected to a second packaging part, which in turn consists of two shell parts mounted pivotally to each other between which the shaft of the item is accommodated and held in a secure position by holding elements.

The holding elements provided for holding the shaft are designed as shell parts that can be locked together pivotable to each other in the area of a film hinge. For complete, touch-proof removal of an item from the packaging, a second film hinge is provided that extends with its longitudinal axis perpendicular to the first-named film hinge. The design of the packaging is expensive, because two pairs of shell parts are present with each pair having a film hinge—connecting each pair—designed pivotal to each other. However, with such sterilizable protective packages the expense associated with this is justified.

To remove the sharp-edged object from the packaging, first the shaft-side snap lock between the shell parts holding and surrounding the instrument shaft there must be released to pivot the two shell parts away from each other. This frees the shaft, and the sharp-edged instrument can only be fixed on an attachment support by a sliding motion.

A rotational movement on the protective packaging to fix the packaged instrument on an external attachment support is not possible. The axis of rotation with which the instrument together with the protective packaging is rotated is coaxial to the second pivot axis of the film hinge that pivotally connects the two shell parts with each other.

A rotational movement to fix the instrument would therefore pivot the two shell parts away from each other as an opening movement and unintentionally open them. This can only be prevented by applying a strong locking force on the two shell parts still closed with the hand performing the rotational movement, but this exposes the packaging to a high torque in the area of the shell parts that twists the two shell parts against each other and unintentionally opens them.

Accordingly, the intended fastening of an instrument can only occur with a sliding motion on the protective packaging in the direction of an external tool holder. After successful fastening, the shell parts accommodating the sharp-edged part of the instrument are pivoted away from each other, which fixes the sharp-edged instrument on the tool holder protected against contact.

A disadvantage of the known packaging is the expense of designing the package with two shell part pairs and the use of two film hinges perpendicular to each other. Another disadvantage is the cumbersome handling, because to release the shaft one shell part pair must first be opened and then the second shell part pair opened for complete removal of the object. The known protective packaging also has no mounting and removal function with which the touch-proof instrument or the item to be held can be attached to and removed from an external tool holder using a rotational movement.

Consequently, the present invention is based on the object of refining a protective packaging of the type described above for any items to be protected in such a way that the object contained in the protective packaging can be mounted on and removed from any fastening holders without contact with the hand and the handling of the protective packaging is simplified.

SUMMARY OF THE INVENTION

To achieve the stated object, the invention is characterized by the technical teaching of a protective packaging with mounting and removal function wherein sharp-edged objects (17) like tools, instruments, holding and fastening means, and the like, are held in a secure position in the packaging. The packaging is at least partly of plastic and includes two shell parts (2, 3) that are connected pivotally on one side with each other in the area of a pivot axis (5a, 5b) to form a first receiving space (8). The object that is being held and protected projects with a free space (36) for the shell parts (2, 3). Inside the shell parts (2, 3), the first receiving space (8) is connected to a second receiving area (56) in which the object (17) that is being held is held form-fitting. Inside the shell parts (2, 3) and the second receiving area (56) there is connected to the second receiving area a third receiving space (57) into which the object (17) projects with the shaft and a tool holder (38) of the object arranged thereon.

The protective packaging (1) is designed as a mounting and removal tool rotatable around its longitudinal axis (55), and that the object (17) contained in the protective packaging (1) can be mounted on and removed from any tool holder (38) together with the protective packaging (1) without contact with the hand.

The invention thus for the first time offers the possibility to accommodate rotation-symmetrical objects, in particular cylindrical objects, and above all rotatably drivable tools and instruments, in the protective packaging and mount them on and remove them from an external tool holder maintaining the secure position in the protective packaging.

The invention is not limited to such tools and instruments. Any other objects can be used, such as screws, pins and other mounting means dependent on a rotatable mounting and removal. However, for simpler depiction only rotatably-drivable tools are referenced in the following description even though the invention is not limited to these.

Such rotatably-drivable tools and instruments are mainly drills, cutters, deburring tools and the like, which are driven rotatably around their longitudinal axis and for this purpose can be mounted in and removed from a rotatably-driven tool holder.

A feature of the invention is that the protective packaging consists of two shell parts pivotal on their face side and connected with each other whose pivot axis is oriented perpendicular to the longitudinal and rotational axis of the packaging.

The result is that a torque exerted with the hand on the protective packaging around its longitudinal axis no longer results in an unintended opening of the two shell parts as was the case in the prior art, because the pivot axis between the two shell parts is now oriented perpendicular to the axis of rotation. In this way, a high insertion and removal torque can be exerted on the protective packaging without it deforming or twisting.

The object to be protected is adapted to the protective packaging such that—viewed in the axial direction of the object—the sharp-edged or otherwise sensitive (first) area of the item is accommodated in a large enough first receiving space (8 and/or 9) of the protective package so that this (first) area of the object can no longer come into contact with the inside of the package in this area.

Attached to this first accommodation area of the protective packaging in the axial direction is a second accommodation area (second receiving area 56) that serves for form-fitting holding of the object in the protective packaging.

In a preferred embodiment of the invention, it is provided that the form-fitting bracket is designed as a clamp bracket for the object being held. In the design as form-fitting holder, it is preferred if this second accommodation area of the protective packaging is designed as a key part that with suitable, multiple-edge bearing surfaces fits an associated key width of the object being held. If the form-fitting holder is additionally designed as clamping, a clamping force is additionally exerted through the bearing surfaces of the object being held that contact it there form-fitting.

This gives the protective packaging a mounting and removal function that previously was not known in protective packages. It therefore functions as a (mounting and removal) tool for manipulating the object contained in the protective packaging.

The third accommodation area of the protective packaging (third receiving space 57), which connects to the second area (second receiving area) in the axial direction, is designed as a collar, by which the shaft of the tool extends radially maintaining a distance and preferably projects over the edge of the collar to guarantee an easy coupling of the tool part projecting from the collar with an external tool holder.

The shaft of the tool is thus designed as a receiving, plug, screw or snap-in area with which the object—while keeping the holder in the protective packaging—can be mounted on a holder arranged outside the protective package of any device, operating area, tool holder, or the like.

The third area (receiving space) of the protective packaging is adapted to the object such that the third area of the protective packaging gives the shaft of the object with its receiving, plug, screw or snap-in area enough room that the object, while maintaining the holder in the protective packaging—handling only the protective packaging—can be introduced into an opposite holder of any machine, an operating area, or any other place of a device and held there.

The invention's protective packaging accordingly has the following functions:

1. Protection of a sensitive or possibly injury-causing object in the protective packaging.

2. Possibility of manipulating the object while maintaining the protection in the packaging by attachment to an external fastening holder.

3. After the object is attached to the external fastening holder, the package is opened by opening the two shell parts pivotally connected with each other and the protective packaging thus opened is now removed from the object attached on the outer fastening holder.

(Mounting Function)

4. To remove an object held in an external fastening holder, the opened protective packaging is put onto the object held in the external tool holder, with the one shell part with its form-fitting and/or clamp holder fitting in the object's key width. The protective package is then closed by the other shell part being unfolded on the shell part already fastened on the object so that its clamp holder at least partly encompasses the object at its key width on the outer circumference. Now the protective package can be grasped with the hand and the object contained in the package released from the attachment support by manipulating the packaging (e.g. by rotating, pushing or the like).

5. The third end of the object with its receiving, plug, screw or snap-in area preferably projects from the upper part of the protective packaging to facilitate the insertion, rotation or other mounting of this object on an opposite support. This area of the protective packaging is designed as a collar area, preferably covered by a protective cap that can be plugged or screwed on when the shell parts are closed.

It is thus provided that on the front side the protective packaging is covered by a sealing cap, with the sealing cap connected with the protective packaging so it can be easily loosened.

In a first preferred embodiment, it is provided that the sealing cap can be snapped onto the protective packaging friction-locking with associated snap-in devices.

In another embodiment, it can be provided that the sealing cap is fastened on the protective packaging with the help of a screw coupling, and in a third embodiment it can be provided that the sealing cap is designed as elastically flexible and elastically expandable. By elastic deformation, it can be put onto the upper front side of the protective packaging.

When the sealing cap is removed, the object being kept in the protective packaging can be free at least in its third (retention, insertion, screw or snap-in) area. It is only when the protective cap is removed that the two shell parts can be pivoted away from each other.

In one preferred embodiment, it is provided that the retention, insertion, screw or snap-in area of the object being protected is now accessible for mounting in an opposite support when the sealing cap is removed. However, this area must not be touched with the hand.

The part of the object being held (the retention, insertion, screw or snap-in area) that becomes free when the sealing cap is removed can be inserted into an opposite support or otherwise manipulated in order to guarantee a touch-proof manipulation of the object in the protective packaging safeguarded against damage, while the object may not be contacted during the mounting and removal of the object still contained in the packaging.

This takes higher safety requirements into consideration, because with sharp-edged or touch-sensitive objects in particular it is no longer necessary to take the object completely out of the protective packaging and only grasp it and manipulate it at will after it is removed from the packaging.

Instead, the invention provides that the protected object remains in the protective packaging and with its end (third area) projecting from the packaging is introduced into a particular receiving device, such as a tool spindle, operation opening, or any other fastener.

Once the protected object is fastened touch-proof on the opposite part together with the protective packaging freed from the protective cap, the packaging can be completely removed.

In a preferred embodiment, the invention provides here that the protective packaging consists of two shell parts pivotally connected with each other, whereby after the protected object is fastened in the opposite part the one shell part is folded so that the object held is still held only in the other shell part friction-locking and form-fitting.

Thereafter, the other shell part can also be removed from the object fastened on the opposite part by which the protected object was attached to an opposite receiving surface fully touch-proof.

This yields the advantage that sharp-edged tools in particular, as are needed in sliver removal with work pieces like drills, cutters, screws and the like, are protected from contact with their sensitive, possibly sharp-edged surfaces so that the risk of injury when handling such tools is minimized.

In another embodiment, it is provided that the protected object consists of medical devices to be handled contact-free, such as medical screws, pins, surgical devices and the like that must be fastened on an opposite fastening surface without risk of contact with the hand or another object.

Here the invention applies, which designs its protective packaging in the same way as before based on a tool to be protected, by the surgical object, screw, pin or the like to be held being contained in the protective packaging and fastened on the opposite fastening surface of any type before the packaging is then removed.

The invention's folding function of the two shell parts through formation of sufficiently large receiving spaces avoids an accumulation of particles from the protective packaging on the sensitive cutting edges or touch-sensitive surfaces of the protected object.

Accordingly, when the shell parts are opened by unfolding the one part from the other there is not the danger of friction occurring during this folding movement on the object's sensitive surfaces to be protected, in particular on sharp-edged surfaces of a tool. Instead, the protective packaging is sized such that the receiving space the protective packaging forms is wide enough that no parts of the tool that are sharp-edged or must be protected against contact touch the inside of the packaging.

In this way, the two shell parts can be separated from each other by unfolding without a danger that during this unfolding motion parts of the flap halves cling to the surfaces of the object or tool that are sharp-edged or must be protected from contact This is in contrast to a protective packaging in which the item to be held is released by a sleeve or the like being removed from the object held in an axial direction. With this removal motion there is always the risk of particles of the protective packaging clinging to the protected object, in particular a sharp-edged tool, which defeats the protective purpose.

Accordingly, with removal from the object manipulated in the axial direction there is the risk of plastic particles or the like still clinging to the protected object during the removal process. This is dangerous when manipulating instruments, devices and mounting parts necessary in the medical field because plastic particles can be introduced into a wound area.

To fulfill the mounting and removal function of the protective packaging, in a first embodiment it is provided that only the form-fitting and/or clamp holder for the protected object is arranged in a shell part while the other shell part is freed from this form-fitting and/or clamp holder.

This has the advantage that after a protected object is successfully mounted with closed flap halves, the one shell part can now be unfolded from the other and the shell part with the clamp surface still remains connected to the protected object and is only removed thereafter.

The invention is not limited to this. In another design, it can be provided that the clamp surfaces for the clamp mounting of the protected object are arranged in the two opposing shell parts. These clamp surfaces thus complement each other into a clamp mounting fully surrounding the key width of the object to be held, which if necessary can be designed even stronger in the plastic material of the protective packaging and/or reinforced by inserted metal parts.

The mounting and removal function of the protective packaging is provided by the fact that the form-fitting and friction-locking clamp surfaces of the protective packaging serving for the clamp mounting of the object at the same time have a form-fitting connection to associate opposite key widths of the object held.

Instead of the described key width and opposite surfaces fitting it friction-locking and form-fitting in the area of the two shell parts, another form-fitting layout can also be chosen. Such form-fitting layouts are, for example, a feather key connection, so that, for example, there is a protruding feather key arranged in the one shell part that engages an associated groove engaging radially on the outer circumference of the object held and the object is thus also designed rotatable by manipulation or rotation of the protective packaging.

Accordingly, the key part of the mounting and removal function is that at least in one shell part a form-fitting and/or clamp holder is arranged that fits on the opposite ends of the object to be held for the form-fitting and friction-locking engagement on opposite ends of the object held, so that the object held, by manipulation of the protective packaging itself, can for example be screwed into a work piece adapter or released from it.

Since it is preferably provided that the protective packaging as a whole consists of a transparent plastic material and accordingly the two shell parts are also made of a plastic material, of course no high torque can be exerted in the mounting and removal of an object contained in the protective packaging.

In an extension, the invention here provides that the sealing cap previously bridging the collars of the two shell parts can now be fitted on the bottoms of the two shell parts to bridge the pivot connection between the two shell parts in order to press the shell parts together with a strong locking force. In this way, the torque exerted on the two shell parts of the protective packaging can be better transmitted to the object contained between the two shell parts.

In the a third embodiment, it can be provided that the sealing cap is removed but the two shell parts are encompassed by a spring clip that prevents the two shell parts from opening and holds the two shell parts together with a strong spring force in order to use the protective packaging as a turning tool like a torque wrench.

If the protective packaging is used with too high a torque, for example by the object being screwed into an opposite holder with too high a torque, the spring clip comes loose from its friction-locking grip around the shell parts so that the function of a torque wrench with overload protection is fulfilled.

Accordingly, what is characterizing for the invention's features is a protective packaging that protects not only the content from contact and damage but also the user, who is protected in manipulating the protected object at any opposite external receiving surfaces of a tool holder against contact with this object.

The invention is not limited to a protective packaging of two shell parts of a plastic material connected pivotally to each other on their front side. The shell parts can also be designed of a metal material or a metal foil or plastic composite film or of cardboard, wood, or plastic-paper or cardboard compound material. If metal materials are used, an aluminum alloy or steel sheet in particular can be utilized.

In place of a film hinge, which joins the two shell parts together in the area of two pivot axes parallel to each other and spaced apart from each other, other known pivot mechanisms can be used such as—with large protective packages—a piano hinge or generally a pivot hinge.

In a preferred embodiment, it can be provided that the two shell parts for the purpose of mutual centering in the folded state have centering surfaces and centering projections opposite each other and engaging each other in the folded state.

However, the invention is not limited to this. Such centering arrangements can also be dispensed with.

In a refinement of the invention, it can also be provided that the two shell parts are designed lockable to each other so that they can only be mutually opened by releasing a snap-in device.

There can be gripping grooves arranged on the sealing cap, and centering ribs can be arranged inside the sealing cap that facilitate centered placement on the collar area of the two shell parts closed against each other.

There can also be one or more locking nubs inside the sealing cap that work with associated locking recesses in the collar area of the two shell parts closed against each other so that the sealing cap can only be removed by overcoming a retaining resistance of the collar area of the two folded shell parts.

In a preferred embodiment the protective packaging has a square profile, which means that the shell parts are mirror-symmetric to each other and each shell part forms, for example, a U-shaped profile so that the two profile halves form a rectangular profile.

The invention is not limited to this. The two shell parts can also consist of a semicircular profile so that the protective packaging formed from them has a round-profile outer circumference.

It is also possible to profile the shell parts in any other manner; for example, oval, multi-sided, polygonal, or the like.

The inventive subject matter of the present invention results not only from the subject of the individual claims but also from the combination of the individual claims.

All information and features disclosed in the documents, including the summary, in particular the spatial design shown in the drawings, are claimed as essential to the invention, so that individually or in combination they are new over the prior art.

Below, the invention is explained based on drawings representing several performance options. Further features and advantages of the invention essential to it emerge from the drawings and their description.

BRIEF DESCRIPTION OF THE SEVERAL VIEWS OF THE DRAWINGS

FIG. 6: closed protective packaging according to FIG. 4 with sealing cap placed on.

DETAILED DESCRIPTION OF THE DRAWINGS

Figure 1:
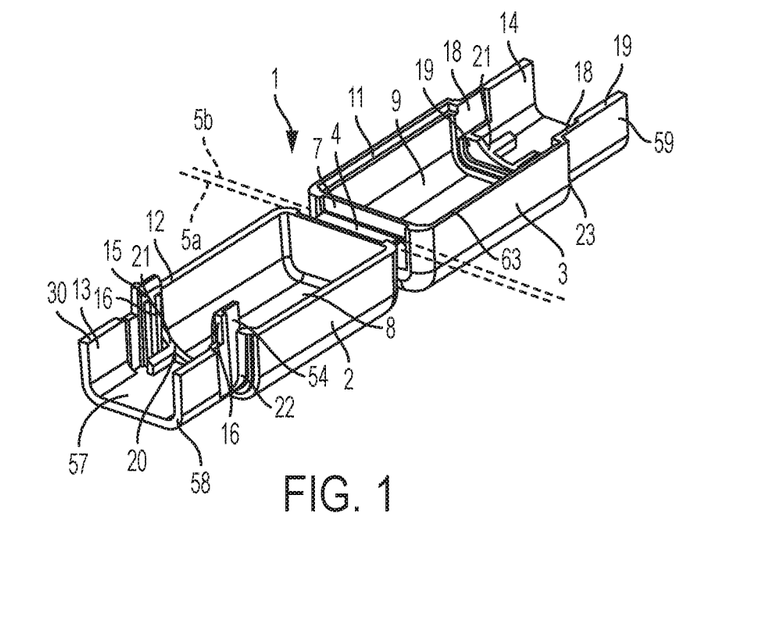
FIG. 1: perspective view of an unfolded protective packaging in a first embodiment.

The protective packaging 1 according to FIG. 1 essentially consists of two shell parts 2, 3 pivotally connected with each other that in the area of two pivot axes 5*a*, 5*b* parallel to each other and spaced opposite to each other are connected with each other pivotally by a film hinge 4. The pivoting occurs by a side of a film hinge 4 joining at the edge the opposite face walls 6, 7 of the two shell parts 2, 3 (at the first ends 60, 61 of the shell parts 2, 3), so that a total of two pivot axes 5*a*, 5*b* are formed parallel to each other and at a mutual distance from each other.

In this way, a certain axial movement play is assigned to the two shells parts 2, 3 during the folding movement (see FIG. 18 and FIG. 20 in arrow direction 44), so that during the folding process a particularly easy centering of the two shell parts 2, 3 is enabled.

Each of the two shell parts 2, 3 forms a first receiving space (8 and/or 9), whereby in the embodiment shown according to FIG. 1 the two shell parts 2, 3 are preferably designed mirror-symmetric to each other so that each receiving space 8, 9 has a roughly equal volume.

However, this is only one embodiment and the invention is not limited to this. It can be provided that the two shell parts 2, 3 are not mirror-symmetric to each other but asymmetrical. The receiving space 8 in the one shell part 2 then has a different volume than the comparative receiving space 9 in the opposite shell part 3.

To enable a centered assembly of the two shell parts 2, 3, it is shown in the embodiment according to FIG. 1 that the longer side walls of the shell part 3 lying opposite each other each forms a receiving slot 11, in which the opposite edge of the shell part 2 designed as centering surface 12 can be introduced in order to center the two shell parts 2, 3 to each other in the folded state.

However, the invention can also provide other centering means, as explained later based on FIG. 10.

Centering means can also be dispensed with generally, because the actual centering of the two shell parts 2, 3 in the closed state occurs by a sealing cap 25 that is put on the collar area (collar halves 13, 14).

In the embodiment shown, a key part 15 connects in the axial direction to the receiving space 8 in a shell part 2 that consists of two key ribs 16 lying opposite each other that form bearing surfaces (15) that contact form-fitting the assigned key widths 31 of an object 17 to be held there.

In the embodiment shown, the key part 15 is accordingly formed only in the one shell part 2, while such a key part 15 is missing in the other shell part 3. However, as indicated in the general description, key parts 15 or other suitable bearing surfaces lying opposite each other and complementing each other can also be arranged in the two shell parts.

FIG. 1 shows as another centering means that centering projections 54 are present on the one shell part 2 over the surrounding outer circumference that engage associated centering recesses 18 on the shell part 3, so that the two shell parts 2, 3 are oriented in correct position to each other when folded together.

It is emphasized that only a single centering means present is also possible, or multiple centering means can also be present next to each other and having the same function. The centering means can also be dispensed with.

The face-side boundary of the given receiving space 8, 9 is formed by stop surfaces 19, 20 arranged on the inside, which form outer stop ribs 22, 23 outward that form the mounted stop for the surrounding face sides of the sealing cap 25 to be put on there.

Accordingly, the sealing cap 25 with its inner circumference is put on over the two collar halves 13, 14 form-fitting, expands to elastically cover the plastic material, and centers itself with centering ribs 27 associated with each other in the clearance of the two collar halves 13, 14 when the two shell parts 2, 3 are folded together.

Figure 2:
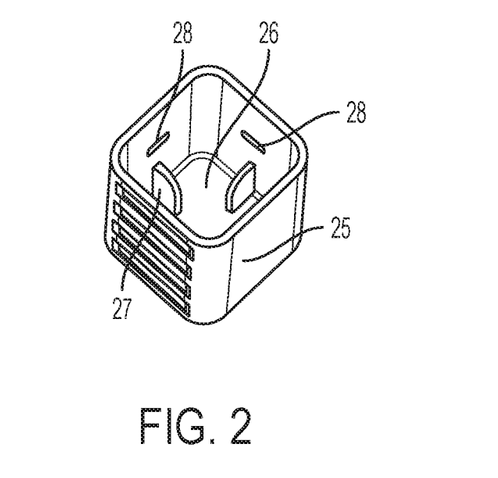
FIG. 2: sealing cap in perspective interior view for sealing a protective packaging according to FIG. 1.
Figure 3:
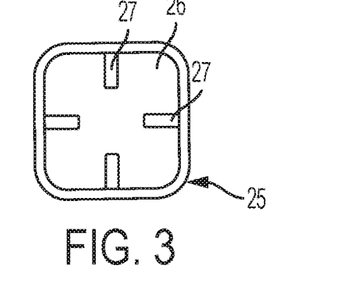
FIG. 3: front view of the sealing cap according to FIG. 2.
Figure 7:
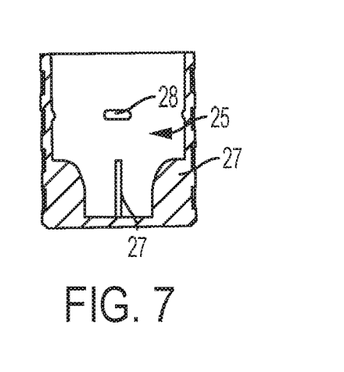
FIG. 7: sealing cap in profile.

According to FIGS. 2 and 7, on the inner surface of the sealing cap 25 there are also locking nubs 28 lying opposite each other that interact with associated locking recesses not shown in the drawings in the area of the two collar halves 13, 14 of the shell parts 2, 3.

Figure 4:
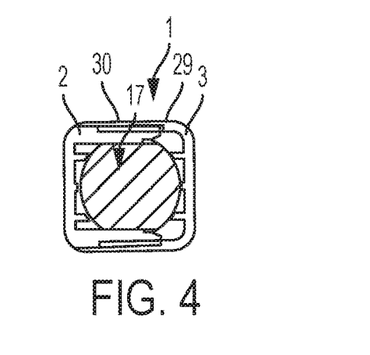
FIG. 4: profile through a closed protective packaging according to FIG. 1 in the straight area.
Figure 6:
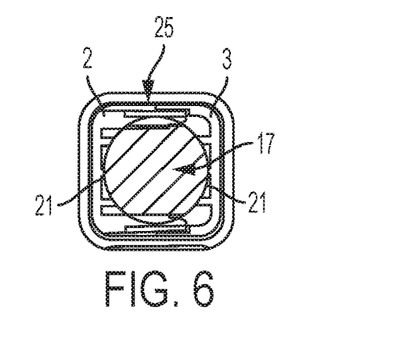

For better fixing of an object 17 to be inserted into the receiving space 8, 9 of the shell parts 2, 3 and protected, on the face-side border of the receiving spaces 8, 9 on the inside there are also seat contours 21 that lie along the outer circumference of the object 17 to be held and protected, as can be best seen from FIG. 4 and FIG. 6.

The sealing cap 25 accordingly forms a mounting reception opening 26, which is placed on the two collars 13, 14 and thus holds the two shell parts 2, 3 securely and protects them against unintended unfolding.

The two shell parts 2, 3 are therefore pressed against each other with a strong locking pressure by the sealing cap 25 and held securely together.

Figure 5:
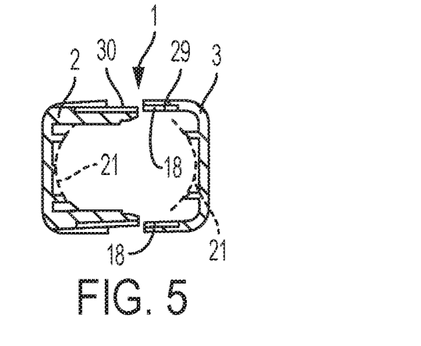
FIG. 5: profile through the protective packaging according to FIG. 1 shortly before the sealing of the two shell parts.

When the two shell parts 2, 3 are folded, there is also a sliding along the two interlocking parts in the area of the collar halves 13, 14, as shown in FIG. 5.

FIGS. 4 and 5 show there are stop surfaces 29 on the one shell part 3 that in the folded state overlap the opposing stop surfaces 30 of the shell part 2 to enable a secure connection between the two shell parts 2, 3 in the folded state.

FIG. 6 further shows how the shell parts 2, 3 secured against shifting are overlapped form-fitting by the sealing cap 25 and thus held together.

Figure 8:
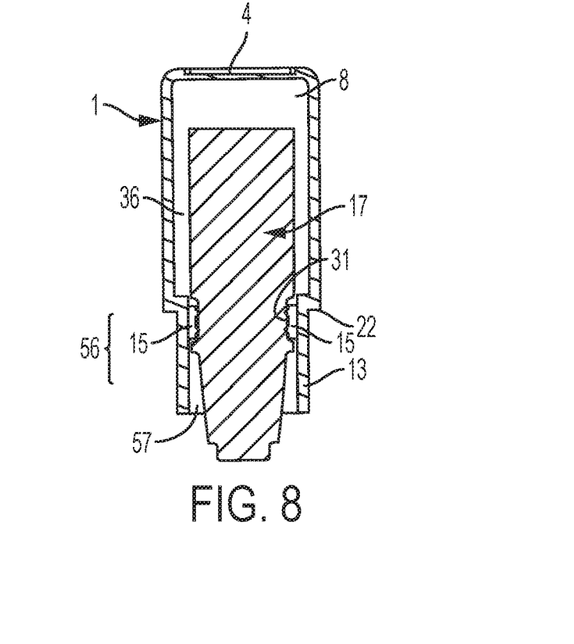
FIG. 8: protective packaging in the folded state with an object contained in it with removed sealing cap.

FIG. 8 shows a protected object 17 that has a radial key width 31 on the outer circumference that is designed, for example, as a hexagon. Also shown is the third receiving area 57 formed in the space provided by the collar halves (13 or 14).

Any mounting tool, such as a wrench, can engage this hexagon.

Instead of a separate assembly tool for mounting an object, the invention's protective packaging 1 is itself designed as an assembly tool.

For this purpose, the protective packaging according to FIG. 1 has key parts 15 adjoining form-fitting the mounting area of the object 17 being assembled. These key parts 15 are bearing surfaces on the package side that interact with associated stop surfaces on the object 17. In the embodiment according to FIG. 1, the bearing surfaces of the key part 15 are designed as key ribs 16, which adjoin the associated bearing surfaces situated opposite them of the object 17 to be held. These bearing surfaces are labeled as key part 15 in the embodiment.

According to FIG. 8, the protective packaging 1 can be rotated together with the object 17 contained there in any manner around its longitudinal axis in order to take the object 17 held form-fitting in the second receiving space (56) in the protective packaging and rotate it in any way if the sealing cap 25 is removed. With this rotation, the tool holder 38 arranged on the object is, for example, screwed into the tool carrier 41 shown in FIGS. 16 to 20.

This special mounting and removal function is addressed further later on based on the other drawings according to FIGS. 15-20.

Figure 9:
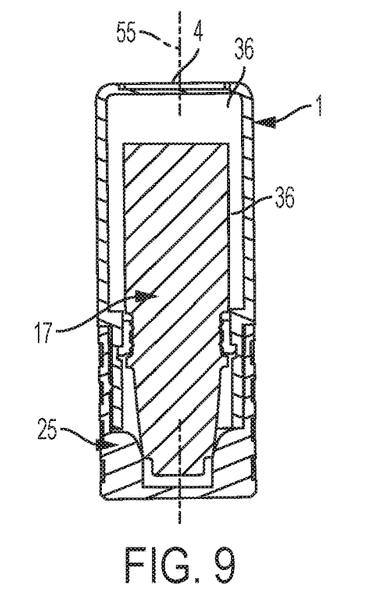
FIG. 9: protective packaging according to FIGS. 7 and 8 with sealing cap placed on in profile.

FIG. 9 shows the finished protective packaging 1 with sealing cap 25 placed on it and containing the object 17 to be protected.

Figure 10:
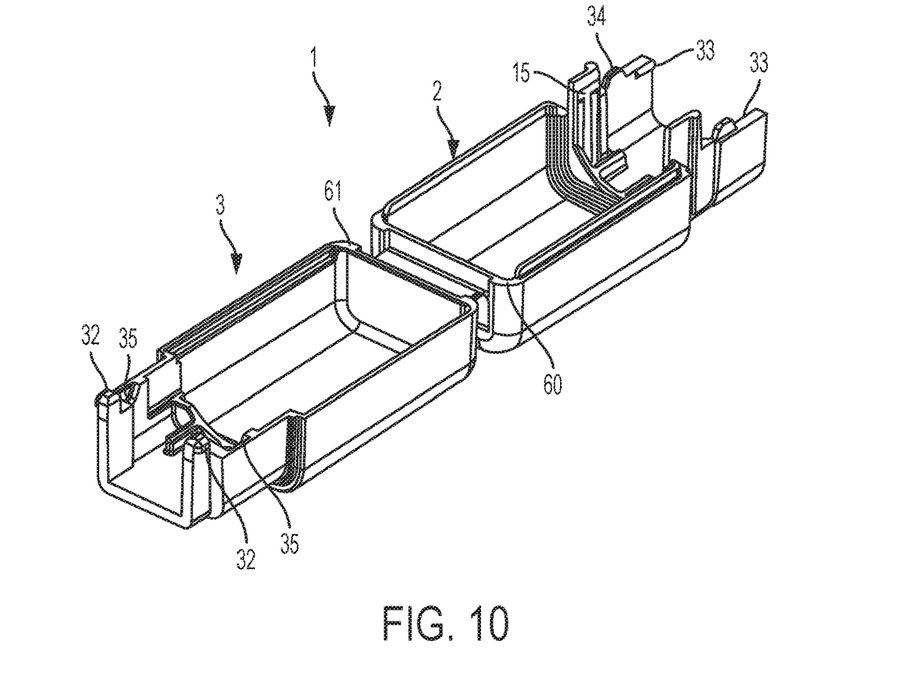
FIG. 10: an embodiment modified relative to FIG. 1 of an unfolded protective packaging in perspective presentation.

In FIG. 10, a different centering of the two shell parts 2, 3 is shown compared with FIG. 1. It is shown there that beyond the key part 15 there are two opposite, outward-directed centering projections 34 on the one shell part 2 that engage the associated centering mount (recess) 35 molded on the other shell part 3 when the two shell parts 2, 3 are connected with each other.

In addition, inward-directed locking projections 33 can be additionally provided on a shell part 2 that interact with associated locking nubs 32 on the opposite shell part 3.

This way, the two shell parts 2, 3 can be connected with each other locking and mutually centering.

Figure 11:
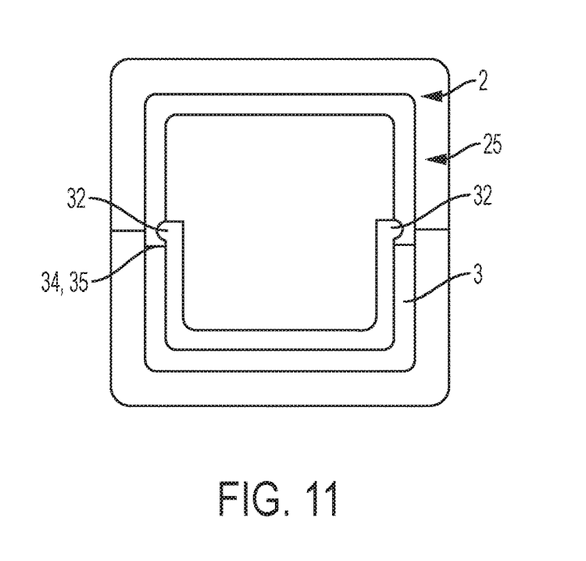
FIG. 11: a profile through the locking level of the protective packaging according to FIG. 10 in the closed state.

FIG. 11 shows the intermeshing locking projections 34, 35 and the locking nub 32 on the one part so it can be seen that there is a centric connection of the two shell parts 2, 3 folded against each other.

Figure 12:
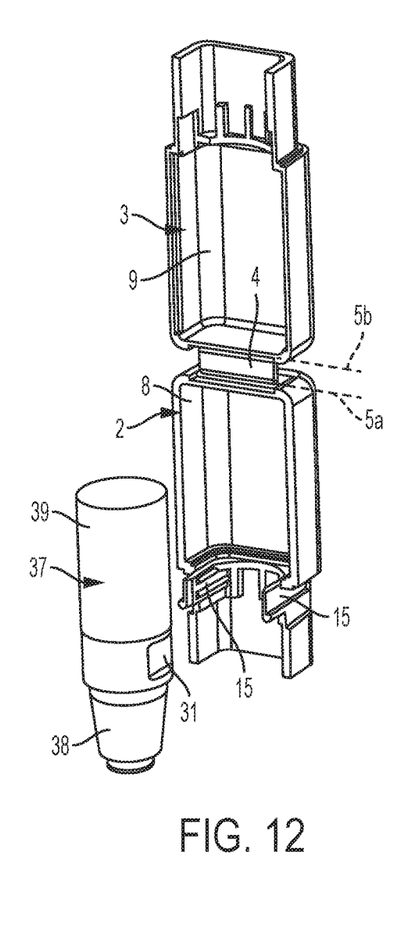
FIGS. 12 to 14: consecutive presentation of the placement of a protected object into a protective packaging according to FIG. 1 or FIG. 10.
Figure 13:
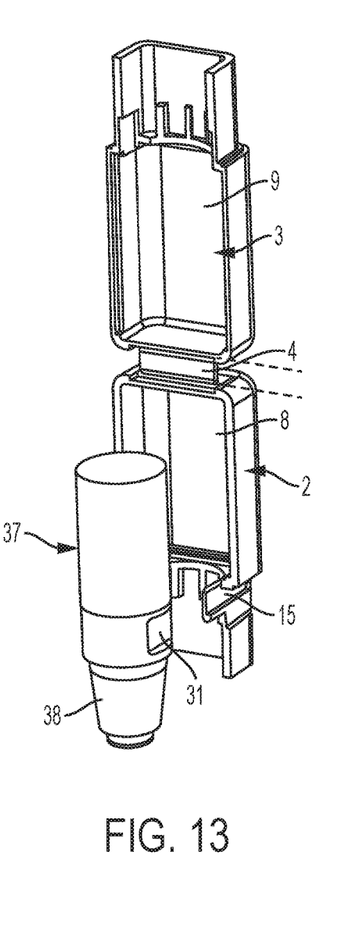
Figure 14:
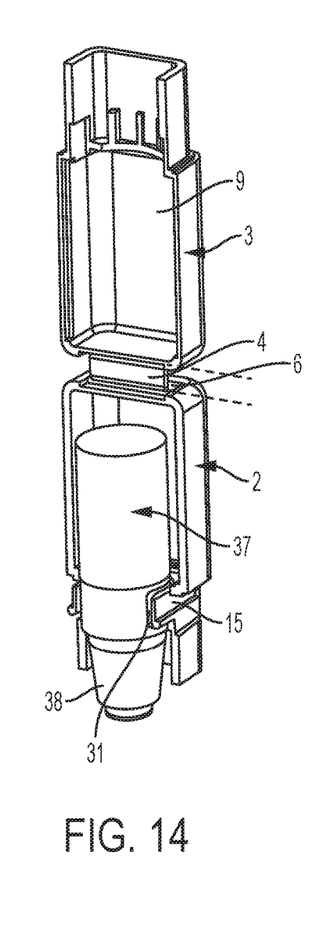

FIGS. 12 to 14 show the mounting process of an object 17 to be held and contained in the protective packaging 1 that is designed by way of example as tool 37 in the embodiment shown.

The tool 37 consists of a cutting part 39 lying above that is touch-sensitive, and contact with which should be avoided. Unintended touching could represent a risk of injury or contamination.

On the lower part of the tool 37 there is a tool holder 38, designed, for example, as a screw thread, plug cone, or lock or clamp projection or the like.

To place such a tool 37 in the protective packaging 1 according to FIGS. 12 to 14, the protected tool 37 is inserted into the protective packaging, as can be seen in the transition from FIG. 12 to FIG. 13, and the key width 31, designed on the tool 37 as, for example, a hexagon, is surrounded by the opposite key parts 15 in a shell part 2 and grasped friction-locking.

Figure 15:
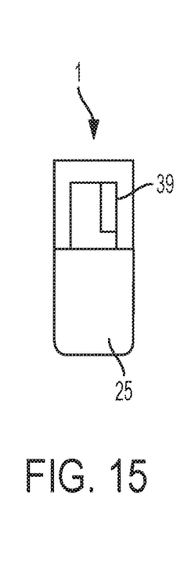
FIGS. 15 to 19: consecutive presentation of the placement of a tool into a protective packaging on an opposite tool holder.

The process is shown once again in FIGS. 15 to 19. Connecting with FIG. 14, FIG. 15 shows that the protective packaging 1 is fully closed by the shell part 3 being folded on the other shell part 2 and the sealing cap 25 then mounted.

FIGS. 16 to 19 show the mounting of a tool 37 fully contained in and protected by the protective packaging on a tool spindle 40 on which a tool carrier 41 is arranged.

Figure 16:
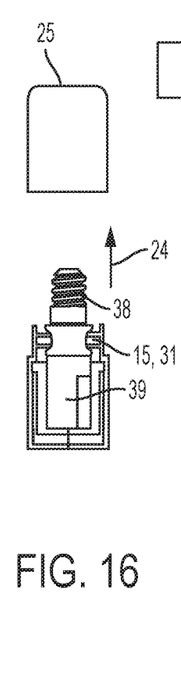
Figure 17:
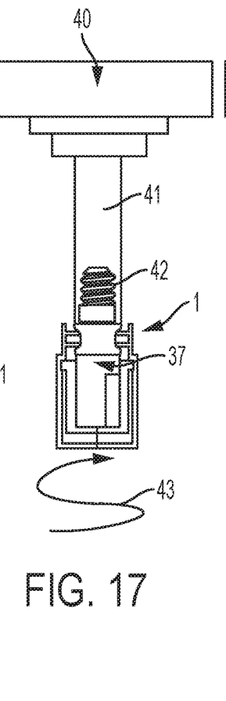

First of all, according to FIG. 16 the sealing cap 25 is removed upward in the direction of arrow 24, as a result of which the upper part of the tool 37, namely the tool holder 38, becomes free when the shell parts 2, 3 are closed. In this position, the protective packaging 1 with the tool 37 lying in it is screwed into the receiving thread 42 on tool carrier 41 through a screw-in motion 43 according to FIG. 17. This thus shows that the protective packaging 1 in the situation according to FIG. 17 simultaneously serves as holder and mounting tool for the tool 37 being screwed in, and at the same time provides the contact protection for this tool 37.

Figure 18:
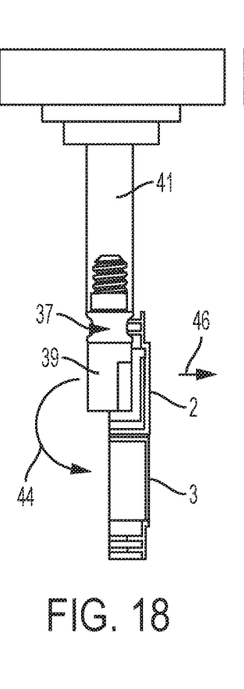

After the tool 37 has been screwed into the receiving thread 42 on the tool carrier 41, the shell part 3 is unfolded downward in arrow direction 44, which frees the one side of the tool 37. The upper shell part 2 can now be removed from tool 37 in arrow direction 46 in a radial direction so that the situation according to FIG. 19 results.

Figure 19:
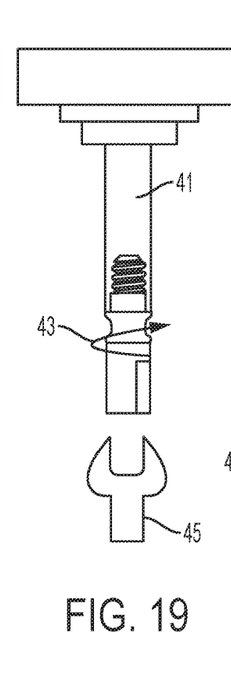

With the protective packaging now removed, tool 37 can be fully screwed into receiving thread 42 on tool carrier 41 with a suitable torque wrench 45.

Figure 20:
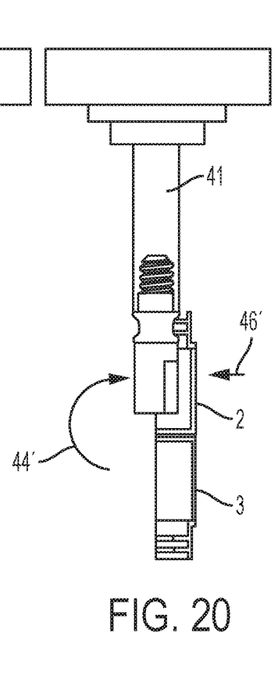
FIG. 20: simplified presentation of the reattachment of the protective packaging with a tool mounted in a work piece adapter.

To remove tool 37 according to FIG. 20, the upper shell part 2 is first mounted onto tool 37 so that key part 15 again is against key width 31 of tool 37 friction-locking. The mounting motion occurs in arrow direction 46'.

After that, the unfolded shell part 3 can be pivoted upward in arrow direction 44' to connect the two shell parts 2, 3 with each other.

With the protective packaging now closed with the two shell parts 2, 3 connected with each other, the tool 37 can now be unscrewed from the receiving thread 42 on the tool carrier 41.

Figures 21, 22, 23:
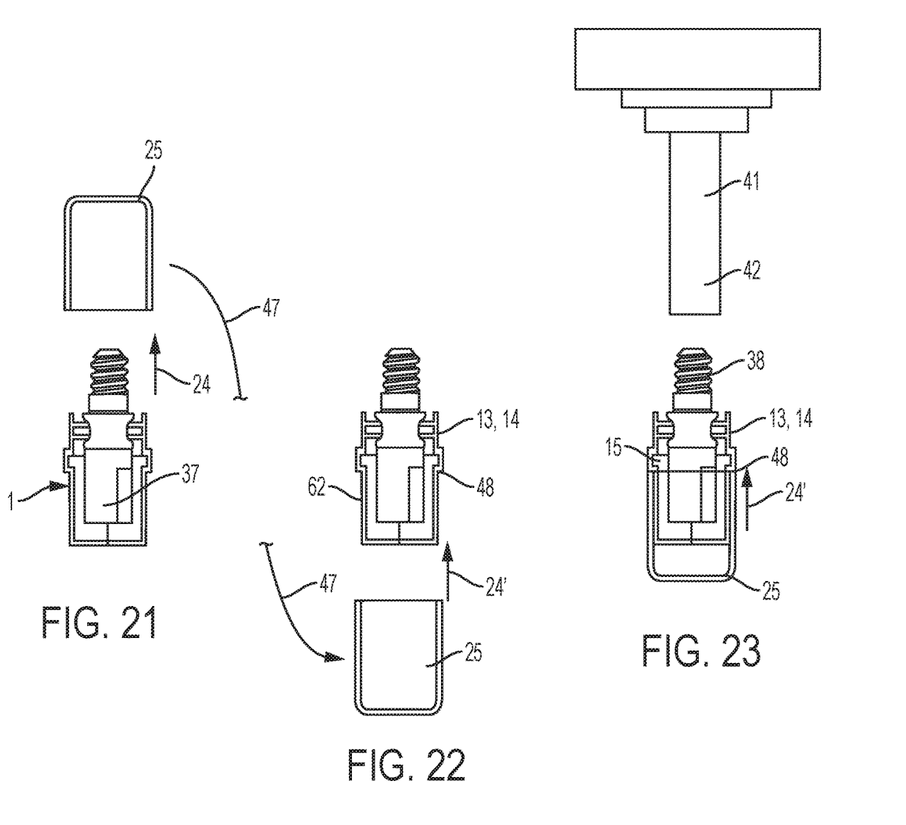
FIGS. 21 to 23: simplified presentation for torque reinforcement of the protective packaging by putting on the sealing cap on the face side.
Figure 24:
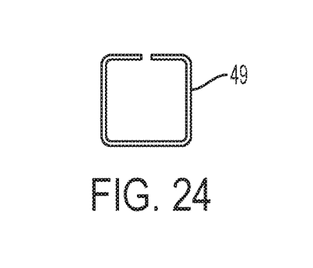
FIGS. 24 to 28: simplified presentation of use of a spring clip for torque reinforcement of the protective packaging.

To strengthen the torque necessary for the unscrewing motion that can be exerted through the protective packaging on a tool 37 contained in it or generally on an object contained in it, FIGS. 21 to 23 provide that the sealing cap 25 can be removed and placed in arrow direction 47 on the rear part (62) of the shell parts 2, 3.

This improves and increases the pivot cohesion of the two shell parts 2, 3. In this way, a higher torque can be applied. Accordingly, the mounting occurs by grasping the protective packaging with the hand and screwing the tool 37 with its tool holder 38 into receiving thread 42 on tool carrier 41.

To limit the torque exerted by the sealing cap 25 during mounting on the protective packaging 1 in arrow direction 24', a surrounding stop 48 can be provided on the upper end of protective packaging 1 that the front face side of the sealing cap 25 abuts. That is an axial mounting restriction for the sealing cap 25.

The FIGS. 24 to 28 show another embodiment of the torque reinforcement.

Rather than placing the sealing cap 25 on the rear pivoting end of the two shell parts 2, 3, a spring clip 49 is used instead. The spring clip 49 is almost completely closed on the circumference, and has only a continuous axial spring gap 50 on the sides that spring-loads against each other the separated halves of spring clip 49.

Figure 25:
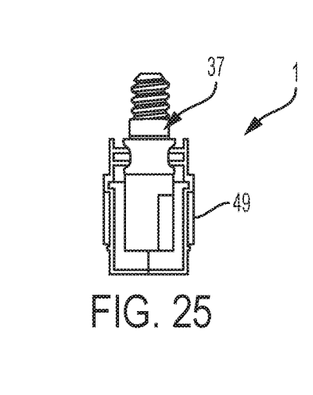
Figure 26:
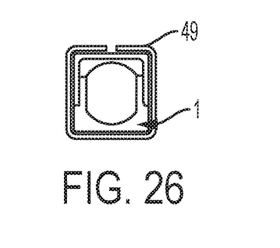
Figure 27:
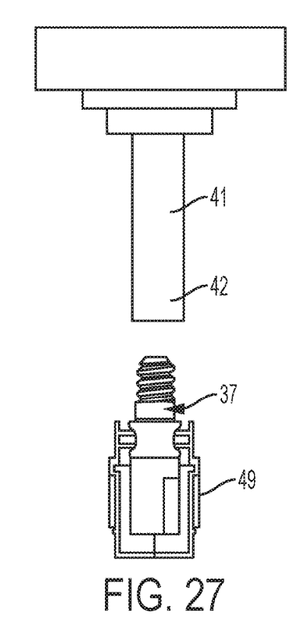

According to FIG. 25, the spring clip 49 is stretched around the outer circumference of the shell parts 2, 3 folded together according to FIG. 25, so that it assumes the shape shown in FIGS. 26 and 27.

In this mounting position, the object 17 arranged in the protective packaging 1 with the spring clip 49 mounted on it can be screwed in or out of the receiving thread 42 and the tool carrier 41 with high torque.

If the insertion or removal torque is exceeded, the key width 31 of the tool 37 attempts to open the pivot connection between the two shell parts 2, 3, but this is prevented by the spring clip 49. However, if the torque becomes too large the key width 31 of tool 37 loosens from the key part 15 of the two shell parts 2, 3. This slippage is perceived acoustically as a grating noise caused by exceeding the insertion or removal torque.

Figure 28:
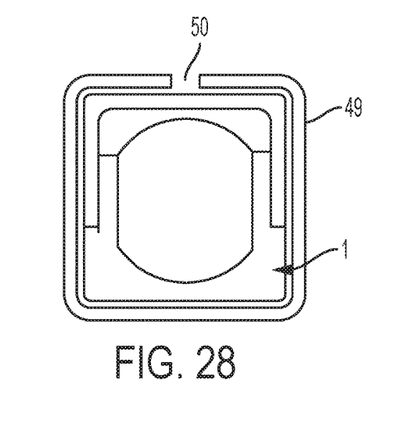

FIG. 28 shows the fully mounted protective packaging.

Figure 29:
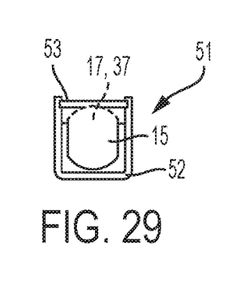
FIG. 29: an embodiment changed relative to the above embodiments of a protective package with a U-profile body of a protective package and a slide cover that can be slid onto it.

FIG. 29 shows an embodiment of a protective packaging modified relative to the previous designs that essentially consists of a U-profile of a plastic body closed on at least one front side, thus freeing on the other front side a tool 37 or object 17 being held. The U-profile is closed by a slide cover 53.

The object 17 or tool 37 being held can only be taken out when the slide cover 53 is removed. So long as the slide cover 53 is slid open, it acts—as in the previous embodiments—like key part 15, which lies form-fitting and friction-locking along the key width 31 of the object held 17, 37 so that this protective packaging 51 can also be used for mounting and removal of an object 17, 37 contained there.

DRAWING LEGEND

1 Protective packaging
2 Shell part
3 Shell part
4 Film hinge
5 Pivot axis 5*a*, 5*b*
6 Face wall (of 2)
7 Face wall (of 3)
8 Receiving space (of 2)
9 Receiving space
10 Shoulder
11 Receiving slot (in 3)
12 Centering surface (in 2)
13 Collar half (of 2)
14 Collar half (of 3)
15 Key part
16 Key rib
17 Object
18 Centering recess
19 Stop surface (in 3)
20 Stop surface (in 2)
21 Seat contour
22 Outer stop rib (in 2)
23 Outer stop rib (in 3)
24 Arrow direction 24'
25 Sealing cap
26 Mounting reception opening
27 Centering rib
28 Locking nub
29 Stop surface (of 14)
30 Stop surface (of 13)
31 Key width (of 17)
32 Locking nub (in 3)
33 Locking projection (in 2)
34 Centering projection
35 Centering mount
36 Free space
37 Tool
38 Tool holder (of 37)
39 Cutting part
40 Tool spindle
41 Tool carrier
42 Receiving thread
43 Screw-in motion
44 Arrow direction 44'
45 Torque wrench
46 Arrow direction 46'
47 Arrow direction
48 Stop
49 Spring clip
50 Spring gap
51 Protective packaging
52 U-profile
53 Slide cover
54 Centering projection
55 Longitudinal axis
56 Second receiving area
57 Third receiving space
58 Second end (2)
59 Second end (3)
60 First end (2)
61 First end (3)
62 Rear part of 2,3
63 Side wall

The invention claimed is:

1. A protective packaging for securing an object used in connection with a holder, the protective packaging configured to maintain the object in a secure position therein, the protective packaging comprising:

first and second shell parts each having a respective face wall, wherein the face walls of the first and second shell parts are pivotally connected to each other with a connection aligned along a pivot axis so that the first and second shell parts can be folded together, and wherein each of the first and second shell parts have respective second ends located opposite from the face walls, the second end of each of the shell parts cooperating to define a collar area at times when the first and second shell parts are folded together;

a first receiving space defined by an inside surface of at least one of the first and second shell parts, the first receiving space adjacent the connection and configured to receive a portion of the object at times when the object is received in the first receiving space;

a second receiving area defined by the at least one shell part, the second receiving area adjacent the first receiving space, wherein the second receiving area defines bearing surfaces configured to engage the object at times when the object is received in the second receiving area;

a third receiving space adjacent the second receiving area and defined by the inside surface of the at least one shell part, the third receiving space configured to receive a portion of the object at times when the object is held in the at least one shell part; and a sealing cap positionable over the collar area and configured to cover a portion of the object at times when the object is received in the first and second shell parts, wherein the protective packaging defines a longitudinal axis and is rotatable about the longitudinal axis.

2. The protective packaging according to claim 1, wherein the connection comprises a film hinge, the film hinge aligned along the pivot axis that is oriented perpendicular to the longitudinal axis of the protective packaging.

3. The protective packaging according to claim 2, wherein the film hinge defines two film hinge pivot axes that are parallel to each other and to the pivot axis, and are a constant distance apart.

4. The protective packaging according to claim 1, wherein an end region of the first and second shell parts adjacent the face walls defines a rear part of the protective packaging, wherein the rear part is configured so that the sealing cap can be placed over the rear part to reinforce a torque strength of the protective packaging.

5. The protective packaging according to claim 1, further comprising a spring clip that, at times when the two shell parts are folded together, stretches partially around the circumference of the two shell parts to spring load the two shell parts against each other to reinforce a torque strength of the protective packaging.

6. The protective packaging according to claim 1, wherein the second receiving area is arranged in only one shell part.

7. The protective packaging according to claim 1, wherein the two shell parts are lockable to each other.

8. The protective packaging according to claim 1, wherein the first and second shell parts have respective centering recesses and centering projections positioned proximal to the second ends thereof, wherein the centering projections are located oppositely from the centering recesses at times when the protective packaging is in a folded position such that the centering recesses and the centering projections mesh with each other to mutually center the first and second shell parts.

9. The protective packaging according to claim 1, wherein one of the first shell part and the second shell part has a receiving slot on a side wall and, at times when the protective packaging is in a folded position, the receiving slot is oriented opposite from a centering surface on the side wall of the other of the first shell part and the second shell part, and wherein the receiving slot and the centering surface cooperate to cause mutual centering of the two shell parts when the first and second shell parts are in the folded position.

10. A protective packaging for securing an object therein, the protective packaging comprising:
   first and second shell parts each having a respective face wall, wherein the face walls are pivotally connected to each other with a connection aligned along a pivot axis that is oriented perpendicular to a longitudinal axis of the protective packaging so that the first and second shell parts can be folded together, and wherein each of the first and second shell parts have respective second ends located opposite from the face walls, the second end of each of the shell parts cooperating to define a collar area at times when the first and second shell parts are folded together; and
   a sealing cap positionable over the collar area and configured to cover a portion of the object at times when the object is received in the first and second shell parts, wherein the collar area includes an outer stop ridge that limits a longitudinal position of the sealing cap,
   wherein an inside surface of at least one of the first and second shell parts defines a space for receiving the object therein, the space including a first receiving space positioned adjacent the face wall and having a first diameter, a third receiving space positioned adjacent the second end, and a second receiving area positioned therebetween, wherein the second receiving area includes seat contours that extend inward from the inside surface and reduce a diameter thereof to less than the first diameter so that the second receiving area is configured to engage the object at times when the object is received in the protective packaging.

11. The protective packaging according to claim 10, wherein the connection comprises a film hinge.

12. The protective packaging according to claim 11, wherein the film hinge defines two film hinge pivot axes that are parallel to each other and to the pivot axis, and are a constant distance apart.

13. The protective packaging according to claim 10, wherein the second receiving area is arranged in only one shell part.

14. The protective packaging according to claim 10, wherein the two shell parts are lockable to each other.

15. The protective packaging according to claim 10, wherein one of the first shell part and the second shell part has a receiving slot on a side wall and, at times when the protective packaging is in a folded position, the receiving slot is oriented opposite from a centering surface on the side wall of the other of the first shell part and the second shell part, and wherein the receiving slot and the centering surface cooperate to cause mutual centering of the two shell parts when the first and second shell parts are in the folded position.

* * * * *